United States Patent [19]
Stepniewski et al.

[11] Patent Number: 5,599,533
[45] Date of Patent: Feb. 4, 1997

[54] STABLE WATER-IN-OIL EMULSION SYSTEM

[75] Inventors: George J. Stepniewski, Melville; Richard A. Konik, Sayville; John D. Dreher, Bay Shore; Gheorghe Cioca, Lake Grove; Isaac D. Cohen, Brooklyn, all of N.Y.

[73] Assignee: Estee Lauder, Inc., New York, N.Y.

[21] Appl. No.: 356,901

[22] Filed: Dec. 15, 1994

[51] Int. Cl.⁶ .................................................. A61K 31/74
[52] U.S. Cl. ........................... 424/78.02; 424/47; 424/59; 424/63; 424/69; 424/401; 514/844; 514/845; 514/937; 514/938; 514/941
[58] Field of Search ...................... 424/78.02, 63, 424/69, 47, 59, 401; 514/941, 937, 938, 844, 845

[56] References Cited

U.S. PATENT DOCUMENTS

| | | | |
|---|---|---|---|
| 4,720,353 | 1/1988 | Bell | 252/309 |
| 4,742,142 | 5/1988 | Shimizu et al. | 528/15 |
| 4,980,167 | 12/1990 | Harashima et al. | 424/401 |
| 5,143,722 | 9/1992 | Hollenberg et al. | 424/63 |
| 5,266,321 | 11/1993 | Shukuzaki et al. | 424/401 |
| 5,441,727 | 8/1995 | Chatterjee et al. | 424/65 |

*Primary Examiner*—Shelley A. Dodson
*Attorney, Agent, or Firm*—Felfe & Lynch

[57] ABSTRACT

Disclosed is a stable water-in-oil emulsion system formed of an organopolysiloxane elastomer, a vehicle in which the elastomer is dispersed or dispersible, a stabilizing agent, a surfactant and an aqueous component and a process for forming the stable water-in-oil emulsion. The stabilized water-in-oil emulsion is useful in personal care products.

40 Claims, No Drawings

STABLE WATER-IN-OIL EMULSION SYSTEM

BACKGROUND OF THE INVENTION

The present invention is a stable water-in-oil emulsion and in particular a water-in-oil emulsion wherein the oil contains as a component one or more organopolysiloxanes and at least one of the organopolysiloxanes is an elastomer.

Emulsions are generally formed from at least two liquid phases which are immiscible so that at least one of the phases is dispersed in fine form throughout the other phase(s). While emulsions are often formed by many components in complex relationships, they can be broadly classified as either oil-in-water or water-in-oil emulsions, depending on which of the phases comprises the dispersed inner phase and which is the continuous outer phase. In this context, an oil may be defined as any material immiscible with water and capable of forming an emulsion with water. Various agents are used to retard or inhibit the separation of emulsions into their constituent phases and these agents may determine the type of emulsion formed. Additionally, the nature of the emulsion can be reversed depending on the agent employed.

Generally speaking, water-in-oil emulsions have been considered less desirable than oil-in-water emulsions because the former have been associated with a greasy feel while the latter are perceived as having a more aesthetically pleasing feel and texture.

Water-in-oil emulsion systems do have desirable properties. However, one drawback to the use of such systems for commercial products is the difficulty associated with maintaining such systems stable against separation.

Irrespective of the desirable properties, unstable compositions of water-in-oil emulsions are of little interest for commercial products. Further, stabilized emulsions which destabilize with the incorporation of customary additives and necessary processing are likewise of little value.

Organopolysiloxanes have, in recent years, gained widespread acceptance and have found a broad spectrum of fields of use such as in, i.e. foodstuffs, medical treatments, personal care compositions including cosmetics, water repellents, lubricants, etc. Within this broad class of materials are compounds known as organopolysiloxane elastomers. While such elastomers have varying and interesting properties, they are often incompatible with other components commonly used in various fields rendering these materials useless or marginally useful for limited applications. Thus it is highly desirable to produce stabilized water-in-oil emulsions wherein the oil component is based on, or comprises, an organopolysiloxane elastomer.

Organopolysiloxanes are a well known class of compounds of the general formula:

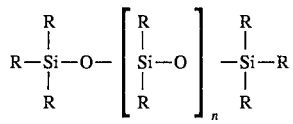

R being the same or different monovalent organic radicals such as alkyl or aryl groups. Organopolysiloxanes are hetero-chain polymers in contrast to those having a backbone which contains only carbon.

SUMMARY OF THE INVENTION

The present invention is a stabilized water-in-oil emulsion and systems incorporating such an emulsion wherein the oil contains as a component one or more organopolysiloxanes at least one of which is an elastomer. The stabilized emulsion contains about 0.1 to 12% of an organopolysiloxane elastomer, about 1 to 90% of a vehicle in which the elastomer is or can be dispersed, and about 0.02 to 40% of one or more stabilizing agents and surfactants, the surfactants having a combined effective HLB of about 2 to 6, with the balance being an aqueous component. The emulsions may contain additional components which would be customary, depending on the field of use. The stabilized emulsions can be used in personal care products such as cosmetics i.e. make-ups, skin creams, and sunscreens.

DESCRIPTION OF PREFERRED EMBODIMENT

The present invention is a stabilized water-in-oil ("w/o") emulsion and more specifically an emulsion wherein the continuous oil phase contains an organopolysiloxane elastomer and the water droplets are dispersed in this oil phase.

The stabilized emulsion contains about 0.1 to 12, and preferably about 0.2 to 4 wt.-% of an organopolysiloxane elastomer, 1 to 90, and preferably 1 to 70 wt. % of a vehicle in which the elastomer is or can be dispersed, about 0.01 to 20 wt.-% of one or more stabilizing agents with the proviso that when one stabilizing agent is used, the preferred range is about 0.1 to 2 wt.-%, and when more than one stabilizing agent is used, each is present in an amount of about 0.1 to 2 wt.-% with the total amounting to about 0.1 to 7 wt.-%, 0.01 to 20 wt.-% of one or more surfactants of a combined effective HLB of about 2 to 6 with the proviso that when one surfactant is used, the preferred amount is about 0.1 to 4 wt.-% and when more than one surfactant is used, each is present in an amount of about 0.1 to 4 wt.-% with the total amounting to between about 0.1 to 20 wt.-% The balance of the composition is an aqueous component.

According to the present invention, the organopolysiloxane is an elastomer. Elastomer compounds are generally chain polymers having a degree of cross-linking sufficient to provide a rubber-like material. Suitable organopolysiloxane elastomers are disclosed in U.S. Pat. No. 5,266,321, the disclosure of which is incorporated herein by reference. The elastomers have a three dimensional cross-linked structure. Other suitable silicone elastomer rubber-like materials are disclosed in U.S. Pat. No. 4,980,167 and U.S. Pat. No. 4,742,142.

In the invention, the organopolysiloxane is an at least partially crosslinked or at least partially cured hetero-chain elastomer. Especially preferred organopolysiloxane elastomeric compounds are those which are at least partially cured addition reaction or products, i.e. hydrosilation products, or addition polymerization products, of an organopolysiloxane having unsaturated groups, such as vinyl or allyl, preferably bonded to at least one terminal Si atom, and another silicon compound capable of participation in the addition reaction such as an organohydrogenpolysiloxane.

The term "oil" as used herein refers to any material which is substantially insoluble in water. When the composition is to be used in a cosmetic or personal care product, the product components must also be cosmetically acceptable or otherwise meet the conditions of the end use product. Suitable oil components include, but are not limited to, natural oils such as coconut oil; hydrocarbons such as mineral oil and hydrogenated polyisobutene; fatty alcohols such as octyldodecanol; esters such as $C_{12}$–$C_{15}$ alkyl benzoate; diesters such as propylene dilarganate; and triesters, such as glyceryl trioctanoate and silicones especially cyclomethicone and dimethicone and mixtures thereof.

According to the present invention, the water-in-oil emulsion contains a vehicle in which the organopolysiloxane can be dispersed. The vehicle is preferably a silicone oil, and most preferably is or includes a volatile silicone oil such as a low molecular weight silicone. Representative volatile silicone substances include cyclomethicone and lower molecular weight dimethicones or mixtures thereof. Particularly preferred as volatile silicone oils are methylated cyclic organpolysiloxanes having ring sizes of 4 to 12, such as octamethylcyclotetrasiloxane, an eight membered ring compound formed from four Si—[CH$_3$]$_2$—O groups and decamethycyclopentasiloxane, a ten membered ring formed from five Si—[CH$_3$]$_2$—O groups. The vehicle can be comprised of a blend or mixture of two or more silicone oils, and may be a blend or mixture of a volatile silicone oil and a non-volatile silicone oil. When the emulsion is so constituted, it contains about 1 to 30 and preferably 10 to 30 wt.-% of a volatile silicone oil and about 10 to 30 and preferably 15 to 20 wt.-% of a non-volatile silicone oil other than the organopolysiloxane elastomer.

The non-volatile non-elastomeric silicone oil can be selected from known products and, for purposes of the present invention, refers to any cosmetically acceptable non-volatile organopolysiloxane including, but not limited to methylated linear polysiloxanes such as higher molecular weight dimethicones; alkylated derivatives of linear polysiloxanes such as cetyl dimethicone and lauryl trimethicone; hydroxylated derivatives of linear polysiloxanes such as dimethiconol; and mixtures thereof. Such silicones generally have a molecular weight of about 100,000 to 1,000,000 and are available commercially from Dow Corning Corporation, Mount Olive, N.J. and GE Silicones, Waterford, N.Y.

The elastomer is dispersed in the vehicle by known homogenization techniques. The dispersion of the elastomer in the vehicle may take on the form of a soft but, stable, viscous gel or stable gel-like material. Gels are generally described as colloids in which a liquid contains a solid arranged in a fine network extending throughout the system. Alternatively, the elastomer already dispersed in the vehicle may be used as a starting material. Dispersions of suitable elastomers in a vehicle are available as Gransil from Grant Industries Inc., Elmwood Park, N.J. The combination of the elastomer and carrier have been found to provide a composition in accordance with the invention having a body but easily applied without a greasy feel.

Stabilizing agents are preferably used in the water phase. Suitable water phase stabilizing agents can include alone or in combination one or more electrolytes, polyols, alcohols such as ethyl alcohol, and hydrocolloids. Preferred electrolytes are alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate. When the stabilizing agent is, or includes, an electrolyte, it amounts to about 0.1 to 5 wt.-% and more preferably 0.5 to 3 wt. % of the total composition. The hydrocolloids include gums, such as Xantham gum or Veegum and thickening agents, such as carboxymethyl cellulose. Polyols, such as glycerine, glycols, and sorbitols can also be used. Preferred polyols are glycerine, propylene glycol, sorbitol and butylene glycol. If a large amount of a polyol is used, one need not add the electrolyte. However, it is especially preferred to use a combination of an electrolyte, a polyol and an hydrocolloid to stabilize the water phase, i.e. magnesium sulfate, butylene glycol and Xantham gum.

Other stabilizing materials can be included such as a high melting point oil material compatible with the oil phase. Suitable materials are fatty esters such as glyceryl tribehenate. Various combinations of the esters and salts can be used.

Other stabilizers include organo-modified clays such as quaternium-18-hectorite.

The one or more surfactants are preferably included as part of the oil phase but may be added or treated as a separate phase. When one surfacant is employed, it preferably has an HLB (hydrophilic-lipophilic balance) of a 2 to 6 and most preferably an HLB of about 2 to 4. Preferably, more than one surfactant is utilized in which case the effective HLB of the combination of surfactants is preferably 2 to 6 and most preferably 2 to 4. Thus, individual surfactants having a higher or lower HLB can be used. Techniques for combining and ascertaining the effective HLB of a mixture of surfactants are known. For an explanation of HLB, see L. M. Prince, in M. G. DeNavarre, "The Chemistry and Manufacture of Cosmetics," Volume III, Second Ed. (Continental Press, Orlando, 1975) at pages 25–37.

Preferred surfactants useful in the invention include those derived from silicone, sorbitan derivatives, and fatty alcohol derivatives. More specifically, suitable surfactants include, but are not limited to, sorbitan sesquioleate, sorbitan oleate, sorbitan isostearate; alkoxylated alcohols such as ethoxylated fatty alcohols including laureth-4, laureth-7, deceth-12, steareth-10; hydroxylated derivatives of polymeric silicones, such as dimethicone copolyol; alkylated derivatives of hydroxylated polymeric silicones such as cetyl dimethicone copolyol; glyceryl esters such as polyglyceryl-4-isostearate; and mixtures thereof, especially mixtures of hydroxylated derivatives of polymeric silicones, alkylated derivatives of hydroxylated polymeric silicones and glyceryl esters, most especially mixtures of dimethicone copolyol, cetyl dimethicone copolyol and polyglyceryl-4-isostearate. Most preferred is a mixture of such surfactants, i.e. a dimethicone copolyol, sorbitan sesquioleate and laureth-7.

The compositions described herein additionally comprise an aqueous component. For purposes of this invention the term "aqueous component" refers to any material consisting essentially of, or predominantly of, water. If used in a cosmetic composition, this component must be a cosmetically acceptable material. The aqueous component of the compositions of the invention serves to increase the water content of the skin and to retard moisture loss from the skin over time.

The aqueous component optionally contains one or more water-soluble emollients including, but not limited to, lower molecular weight aliphatic diols such as propylene glycol and butylene glycol; polyols such as glycerine and sorbitol; and polyoxyethylene polymers such as polyethylene glycol 200. The specific type and amount of water soluble emollient(s) employed will vary depending on the desired aesthetic characteristics of the composition, and is readily determined by one skilled in the art.

The aqueous component preferably is water which is deionized distilled or similarly purified. Preferred stabilized emulsions contain about 10–60 wt.-% and preferably 30–45 wt.-% water.

The stabilized emulsion can be incorporated with other materials or other systems. When used in personal care products, such as cosmetics, the stabilized emulsion as a component of the composition has a broad range and, depending on the number of other components, can constitute 50 to 95, preferably 70 to 90 and most preferably 80 to 90 wt.-% of the cosmetic composition. Other additives can include, depending on the use, glycols, vitamins A and E in their various forms, sunscreen agents, humectants, preservatives, such as known parabens, emollients, occlusive agents, and esters. Other additives can include pigments especially when the emulsion is used as a make-up. Preferred pigments are iron oxides and titanium dioxide which can be present in the composition in the amount of 0.1 to 30 wt.-%, preferably 5 to 20 wt.-% and most preferably 8 to 14 wt.-%.

In producing the stabilized emulsion of the invention, the oil and water phases are formed separately. In a first vessel, the organopolysiloxane elastomer - vehicle dispersion is combined with other components, such as the one or more surfactants which are dispersible in the oil, and subjected to low shear mixing. If the elastomer is not already dispersed in the vehicle, i.e. volatile and/or other non-volatile silicone oils, the elastomer can be dispersed in the vehicle by high speed or homogenous mixing. Preferably, the mixing breaks up the organopolysiloxane until no discrete particles of the elastomer or gel remain. If necessary, the elastomer or gel, can be roller milled or, if mixed with other materials, roller milled in a blended form mixed with the volatile oil. If a fatty ester which is a solid at room temperature is employed to stabilize the oil phase, heat may be required sufficient to reach the melting point of the fatty ester so that satisfactory dispersion of the ester in the oil phase can be achieved.

The water and water compatible stabilizing agents are mixed together under low shear conditions at room temperature. The water mix is then charged, preferably slowly, into the oil phase. Preferably, the two phases are at about the same temperature prior to their inter-mixture under high shear mixing conditions. The phases can also be mixed to form the emulsion at an elevated temperature consistent with that necessary to disperse the fatty ester.

The emulsion of the water and oil phases is subjected to high speed homogenization for about 15 to 30 minutes. The exact amount of homogenization will vary with the final characteristic desired as readily determinable by one skilled in the art but should not be so vigorous as to break-up the emulsion.

Depending on the use of the composition, the other additives may be dispersible in the oil or water phase. Preferably, the additives are incorporated in the appropriate phase before the water mix is charged into the oil phase. In such instances, the oil or water phase is separately mixed or blended with the additives to produce a uniform phase prior to the mixing of the oil and water phase.

EXAMPLE 1

Skin Treatment Cream

A skin treatment cream was prepared by individually preparing each of phase 1, 2 and 3 as set forth below. The weight percentages indicated are based on the final composition.

| Component | Wt. % |
|---|---|
| Phase 1 | |
| Cyclomethicone/Dimethiconol (Dow Corning Q2-1401 Fluid) | 2.00 |
| Octamethylcyclotetrasiloxane Organopolysiloxane (Gransil) | 68.00 |
| Cetyl Dimethicone Copolyol | 0.50 |
| Cyclomethicone (Dow Corning 345 Fluid) | 4.00 |

-continued

| Component | Wt. % |
|---|---|
| Phase 2 | |
| Fruit Extract (Fruit Concentrate AHA-5) (Centerchem, Inc., Stamford CT) | 1.00 |
| Butylene Glycol/Alphahydroxy-decanoic acid/Alphahydroxyoctanoic acid (Michel Mercier Products, Inc.) | 2.00 |
| SD Alcohol 40 | 10.00 |
| Water | 12.00 |
| Tetrahydroxypropyl Ethylenediamine | 0.20 |
| Phase 3 | |
| D&C Violet | .003 |
| Triethyl Citrate | .297 |

Each of phases 1, 2 and 3 was individually formed at room temperature with stirring until homogeneous. Phase 1 was slowly added to phase 2 while the mixture of the phases was being homogenized with a Silverson homogenizer at room temperature. Phase 3 was added to combined phases 1 and 2 and the resulting mixture was homogenized until a smooth consistency was obtained.

The resulting cream was easy to apply, had good tactile properties but no oily feel and exhibited excellent long term stability.

EXAMPLE 2

Cosmetic Foundation

Each of the following phases 1, 2 and 3 was separately prepared by low shear mixing and then combined with high shear blending.

| Component | Wt. % |
|---|---|
| Phase 1 | |
| Cyclomethicone | 16.90 |
| Organopolysiloxane Octymethylcyclotetrasiloxane | 5.00 |
| Cyclomethicone/Dimethiconol | 1.00 |
| Dimethicone Copolyol | 1.50 |
| Sorbitan Sesquioleate | 1.50 |
| Phenyl Trimethicone | 10.00 |
| Dimethicone | 10.00 |
| Phase 2 | |
| Red Iron Oxide coated with Methicone | 0.59 |
| Yellow Iron Oxide coated with Methicone | 1.22 |
| Black Iron Oxide coated with Methicone | 0.13 |
| Titanium Dioxide coated with Methicone | 3.56 |
| Ultrafine Titanium Dioxide coated with Methicone | 4.50 |
| Phase 3 | |
| Water | 37.75 |
| Butylene Glycol | 5.00 |
| Xanthan Gum | 0.10 |
| Magnesium Sulfate | 1.00 |
| Laureth-7 | 0.25 |

The pigment phase is added to the oil phase and mixed at room temperature to form a uniform mixture. Phase 3, the water phase, is slowly added to the mixed oil-pigment phases and homogenized until smooth. The resulting foundation has superior application and tactile properties such as cushion, body and slip, but without a greasy feel.

It will be understood that the specification and examples are illustrative but not limitative of the present invention and that other embodiments within the spirit and scope of the invention will suggest themselves to those skilled in the art.

We claim:

1. A stabilized water-in-oil emulsion, comprising
   a. an organopolysiloxane elastomer present in an amount of about 0.1 to 12 wt.-%;
   b. a vehicle in which the elastomer is dispersed, the vehicle present in an amount of about 1 to 90 wt.%;
   c. at least one stabilizing agent which is an electrolyte, a polyol, an alcohol or a hydrocolloid and mixtures thereof present in an amount of about 0.01 to 20 wt.-%;
   d. at least one surfactant present in an amount of about 0.01 to 20 wt.-%; and
   e. an aqueous component.

2. The emulsion of claim 1 wherein the elastomer is present in an amount of about 2 to 4 wt.-%.

3. The emulsion of claim 1 wherein the elastomer is a reaction product of an organopolysiloxane having an unsaturated group bound to a terminal Si-atom and an organohydrogensiloxane which reaction product is at least partially cured.

4. The emulsion of claim 1 wherein the vehicle is a silicone oil.

5. The emulsion of claim 4 wherein the vehicle is a volatile silicone oil.

6. The emulsion of claim 5 wherein the vehicle further comprises a non-volatile silicone oil other than (a).

7. The emulsion of claim 6 wherein the vehicle comprises about 1 to 30 wt.-% of a volatile silicone oil and about 10 to 30 wt.-% of a non-volatile silicone oil other than (a).

8. The emulsion of claim 5 wherein the volatile silicone oil is present in an amount of 10 to 30 wt.-%.

9. The emulsion of claim 6 Wherein the volatile silicone oil is present in an amount of 10 to 30 wt.-%.

10. The emulsion of claim 7 wherein the non-volatile silicone oil is present in an amount of 15 to 20 wt.-%.

11. The emulsion of claim 5 wherein the volatile silicone oil is at least one selected from the group consisting of cyclomethicone and lower molecular weight dimethicone.

12. The emulsion of claim 1 wherein the least one surfactant is a dimethicone copolyol.

13. The emulsion of claim 11 wherein the cyclomethicone has a ring size of 4 to 12.

14. The emulsion of claim 13 wherein the cyclomethicone is at least one of octamethylcyclotetrasiloxane and decamethylcyclopentasiloxane.

15. The emulsion of claim 1 wherein the least one stabilizing agent is present in an amount of 0.1 to 2 wt.-%.

16. The emulsion of claim 1 wherein the stabilizing agent is at least one of an alkali metal salt, alkaline earth salt, a polyelectrolyte, and thickening agents.

17. The emulsion of claim 1 wherein the least one stabilizing agent is an electrolyte selected from the group consisting of chloride or sulfate salts of sodium, potassium, calcium, magnesium and mixtures thereof.

18. The emulsion of claim 1 wherein the least one stabilizing agent is at least one salt present in an amount of 0.1 to 2 wt.-%.

19. The emulsion of claim 1 wherein the least one surfactant is a water-in-oil emulsifier and has an HLB of about 2 to 6.

20. The emulsion of claim 1 wherein the least one surfactant comprises at least two surfactants and the least two surfactants have an effective combined HLB of about 2 to 6.

21. The emulsion of claim 1 wherein the least one surfactant is at least one of a silicone derivative, sorbitan derivative and a fatty alcohol derivative.

22. The emulsion of claim 1 wherein the aqueous component is water and is present in an amount of about 35 to 45 wt.-%.

23. The emulsion of claim 1 further comprising at least one pigment.

24. A personal care product comprising the emulsion of claim 1.

25. The personal care product of claim 24 further comprising at least one pigment.

26. The emulsion of claim 1 produced by the process comprising: dispersing an organopolysiloxane elastomer in a vehicle with homogenous mixing to form an oil phase; introducing a surfactant; forming an aqueous phase under low shear conditions; introducing the aqueous phase into the oil phase to form a mixture; and subjecting the mixture of the aqueous and oil phases to high speed homogenization.

27. The emulsion of claim 1 produced by the process comprising: combining an organopolysiloxane elastomer - vehicle dispersion with a surfactant to form an oil phase; forming an aqueous phase under low shear conditions; introducing the aqueous phase into the oil phase to form a mixture; and subjecting the mixture of the aqueous and oil phases to high speed homogenization.

28. A stabilized water-in-oil emulsion, comprising:
   a) an organopolysiloxane elastomer present in an amount of about 0.1 to 12 wt.-%;
   b) a vehicle in which the elastomer is dispersed, present in an amount of about 1 to 90 wt.-%, the vehicle comprising octamethylcyclotetrasiloxane;
   c) at least one stabilizing agent which is an electrolyte, a polyol, an alcohol or a hydrocolloid and mixtures thereof present in an amount of about 0.01 to 20 wt.-%;
   d) at least one surfactant present in an amount of about 0.01 to 20 wt.-%; and
   e) an aqueous component.

29. The emulsion of claim 28 wherein the least one surfactant comprises a dimethicone copolyol, sorbitan sesquioleate and laureth-7.

30. The emulsion of claim 28 further comprising at least one pigment.

31. A make-up composition comprising:
   a) an organopolysiloxane elastomer present in an amount of about 0.1 to 12 wt.-%;
   b) a vehicle in which the elastomer is dispersed present in an amount of about 1 to 90 wt.-%;
   c) at least one stabilizing agent which is an electrolyte, a polyol, an alcohol or a hydrocolloid and mixtures thereof present in an amount of about 0.01 to 20 wt.-%;
   d) at least one surfactant present in an amount of about 0.01 to 20 wt.-%; and
   e) at least one pigment; and
   f) an aqueous component.

32. The make-up composition of claim 31 wherein the least one pigment includes at least one of a iron oxide and titanium dioxide.

33. A process of producing a stabilized water-in-oil emulsion comprising: dispersing an organopolysiloxane elastomer in a vehicle with homogenous mixing to form an oil phase; introducing a surfactant; forming an aqueous phase under low shear conditions; introducing the aqueous phase into the oil phase to form a mixture; and subjecting the mixture of the aqueous and oil phases to high speed homogenization.

34. A process of producing a stabilized water-in-oil emulsion comprising: combining an organopolysiloxane elastomer - vehicle dispersion with a surfactant as an oil phase; forming an aqueous phase under low shear conditions; introducing the aqueous phase into the oil phase; and subjecting the mixture of the aqueous and oil phases to high speed homogenization.

35. The stabilized water-in-oil emulsion of claim 1 wherein the vehicles comprises a silicone oil.

36. The stabilized water-in-oil emulsion of claim 28 wherein the least one surfactant is selected from the group consisting of sorbitan sesquioleate, sorbitan oleate, sorbitan isostearate, alkoxylated alcohols, ethoxylated fatty alcohols, hydroxylated derivatives of polymeric silicones, alkylated derivatives of hydroxylated polymeric silicones, glyercyl esters, and mixtures thereof.

37. The stabilized water-in-oil emulsion of claim 1 wherein the least one stabilizing agent is a mixture of magnesium sulfate, butylene glycol and Xantham gum.

38. The stabilized water-in-oil emulsion of claim 21 wherein the least one surfactant is a mixture of dimethicone copolyol, sorbitan sesquioleate and laureth-7.

39. The stabilized water-in-oil emulsion of claim 16 wherein the stabilizing agent is at least one of the the borate and citrate salts of sodium, potassium, calcium and magnesium, aluminum chlorohydrate, a polyelectrolyte and a thickening agent, hyaluronic acid, sodium hyaluronate, Xantham gum, Veegum, carboxymethyl cellulose, glycerine, glycols, sorbitols, propylene glycol, and butylene glycol.

40. The stabilized water-in-oil emulsion of claim 28 wherein the least one surfactant is selected from the group consisting of laureth-4, laureth-7, deceth-12, steareth-10, dimethicone copolyol, cetyl dimethicone copolyol, and polyglyceryl-4-isostearate.

* * * * *

UNITED STATES PATENT AND TRADEMARK OFFICE
CERTIFICATE OF CORRECTION

PATENT NO : 5,599,533
DATED : February 4, 1997
INVENTOR(S): Stepniewski et al.

It is certified that error appears in the above-identified patent and that said Letters Patent is hereby corrected as shown below: On the title page: Item [75]

Joan N. Phillips, of Dix Hills, N.Y. and Julius R. Zecchino, of Closter, N.J. should be added as co-inventors.

Signed and Sealed this

Twenty-eighth Day of April, 1998

Attest:

BRUCE LEHMAN

*Attesting Officer*

*Commissioner of Patents and Trademarks*